(12) United States Patent
Lumpkin

(10) Patent No.: US 8,657,784 B1
(45) Date of Patent: Feb. 25, 2014

(54) CATHETER STOP

(76) Inventor: Jane Terri Lumpkin, Fort Worth, TX (US)

(*) Notice: Subject to any disclaimer, the term of this patent is extended or adjusted under 35 U.S.C. 154(b) by 386 days.

(21) Appl. No.: 13/024,427

(22) Filed: Feb. 10, 2011

Related U.S. Application Data

(60) Provisional application No. 61/303,026, filed on Feb. 10, 2010.

(51) Int. Cl.
*A61M 5/00* (2006.01)

(52) U.S. Cl.
USPC ............................................ 604/117

(58) Field of Classification Search
USPC ............... 604/117, 158; 128/207.14, 207.15
See application file for complete search history.

(56) References Cited

U.S. PATENT DOCUMENTS 7,458,955 B2 * 12/2008 Owens et al. ................ 604/117

* cited by examiner

*Primary Examiner* — Theodore Stigell
(74) *Attorney, Agent, or Firm* — Kenneth L Tolar

(57) ABSTRACT

A catheter stop includes an obstruction attached to a catheter at a location that represents the maximum acceptable insertion depth of the catheter into a tracheal tube without causing damage to a patient or the tube. In one embodiment, the obstruction is a pad having a pair of opposing adhesive wings for securing the pad to the catheter. In another embodiment, the obstruction is formed of a triangular housing having a pair of hinged sections that open and close in a clamshell-type fashion. Each section includes a longitudinal, semi-cylindrical, bore that cooperates with the bore on the other section to form a tubular passageway for accommodating the catheter when the sections are closed. A clamp on an edge of one section detachably engages a latch on the corresponding edge of the other section to secure the housing about the catheter.

10 Claims, 4 Drawing Sheets

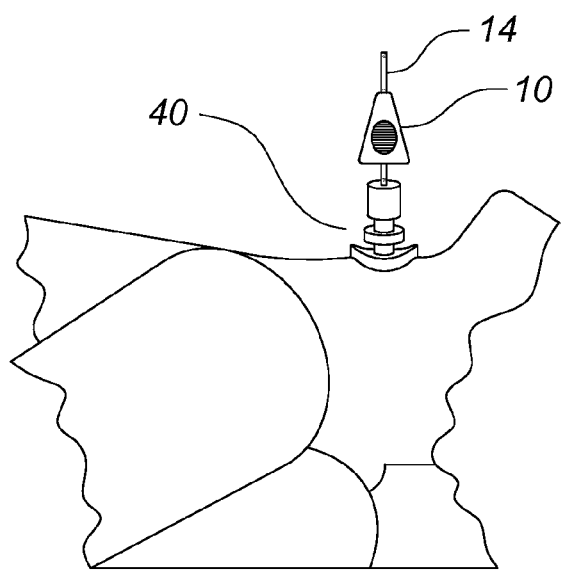
Fig. 5
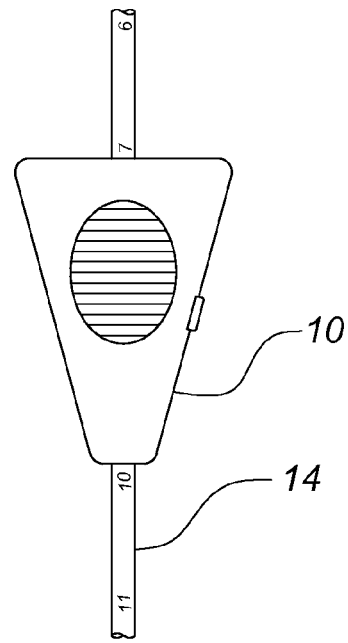
Fig. 6
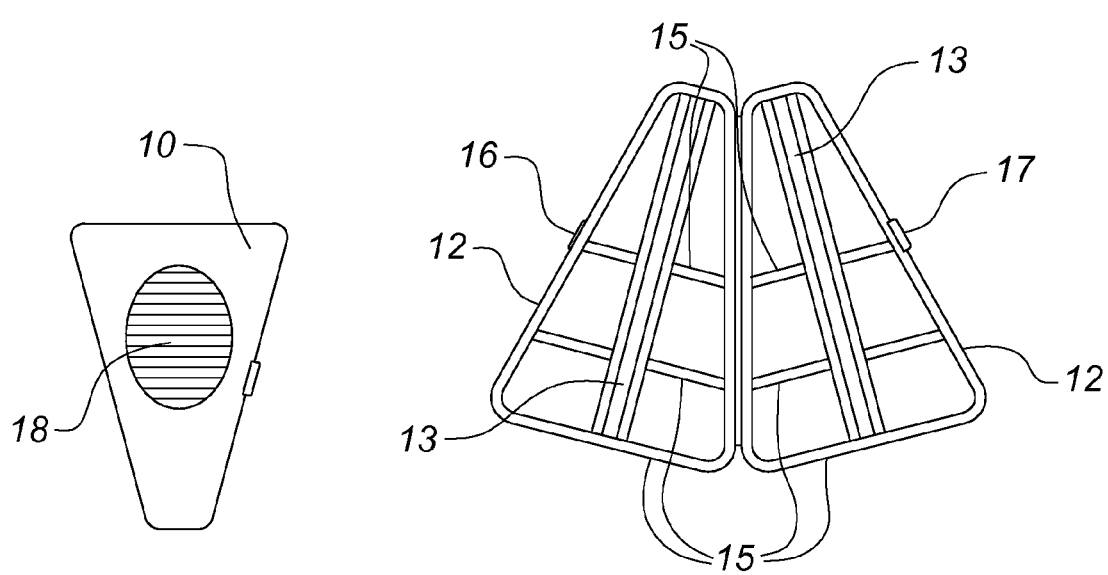
Fig. 8
Fig. 7

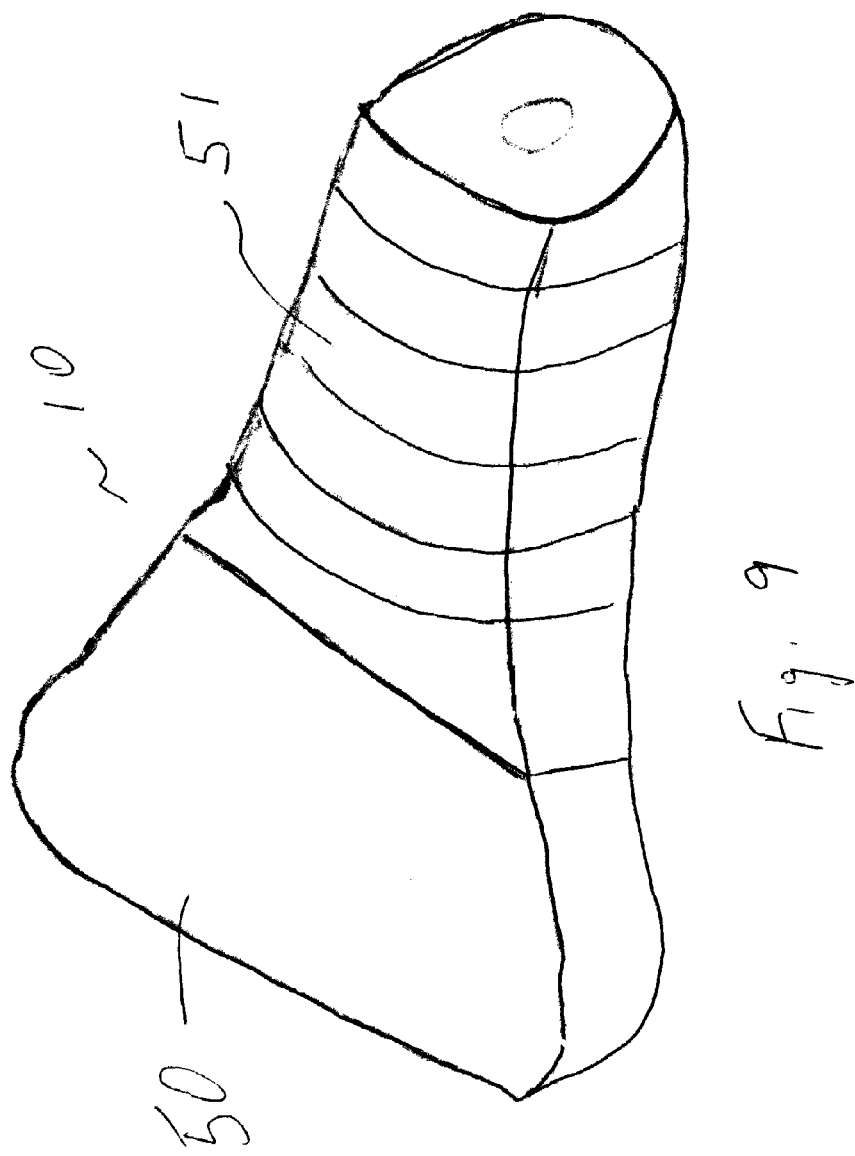

CATHETER STOP

CROSS REFERENCE TO RELATED APPLICATIONS

This application is entitled to the benefit of provisional application No. 61/303,026 filed on Feb. 10, 2010, the specification of which is incorporated herein by reference.

BACKGROUND OF THE INVENTION

The present invention relates to a device that limits the insertion depth of a suction catheter.

DESCRIPTION OF THE PRIOR ART

In certain medical situations, a tracheal or tracheostomy tube is inserted into a patient's trachea to maintain adequate respiration. Often, a suction catheter must be inserted into the tube to remove respiratory secretions. However, the caregiver can overextend the suction catheter, causing damage to the tube or the patient. Accordingly, there is currently a need for a device that prevents a suction catheter from being overextended into a tracheal tube. The present invention addresses this need by providing a stop that is selectively attachable to a suction catheter to minimize the insertion depth thereof.

SUMMARY OF THE INVENTION

The present invention relates to a catheter stop comprising an obstruction attached to a catheter at a location that represents the maximum acceptable insertion depth of the catheter into the tracheal tube. In one embodiment, the obstruction is a pad having a pair of opposing adhesive wings for securing the pad to the catheter. In another embodiment, the obstruction is formed of a triangular housing having a pair of hinged sections that open and close in a clamshell-type fashion. Each section includes a longitudinal, semi-cylindrical, central bore that cooperates with the bore on the other section to form a tubular passageway when the sections are closed. The passageway is dimensioned to lightly grip a suction catheter having a discrete diameter. A clamp on an edge of one section detachably engages a latch on the corresponding edge of the other section to secure the housing about a suction catheter. Accordingly, a caregiver determines the position on the suction catheter that represents the maximum acceptable insertion depth. The housing sections are fastened about the catheter at the selected position to prevent the catheter from being extended beyond the maximum acceptable insertion depth.

It is therefore an object of the present invention to provide a device that prevents a suction catheter from being overextended within a tracheal tube.

It is another object of the present invention to provide a stop that is easily securable to a suction catheter.

Other objects, features, and advantages of the present invention will become readily apparent from the following detailed description of the preferred embodiment when considered with the attached drawings and the appended claims.

BRIEF DESCRIPTION OF THE DRAWINGS

FIG. 5 depicts a suction catheter inserted into a patient with the stop according to a second embodiment of the present invention mounted thereon.

FIG. 6 is a front, plan view of the stop depicted in FIG. 5 secured to a suction catheter.

FIG. 7 depicts the housing in an open configuration.

FIG. 8 is an isolated view of the housing.

FIG. 9 depicts a third embodiment of the present invention.

DESCRIPTION OF THE PREFERRED EMBODIMENT

Figure 1:
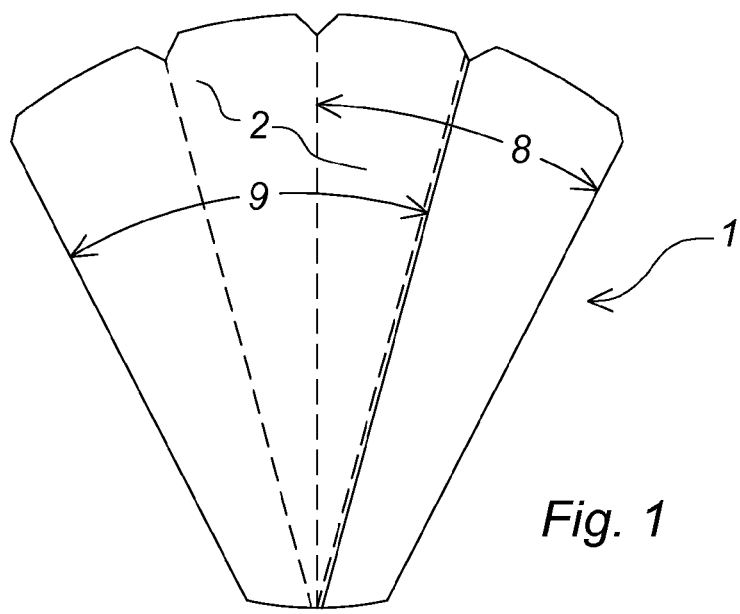
FIG. 1 is a plan view of the catheter stop according to a first embodiment of the present invention.
Figure 2:
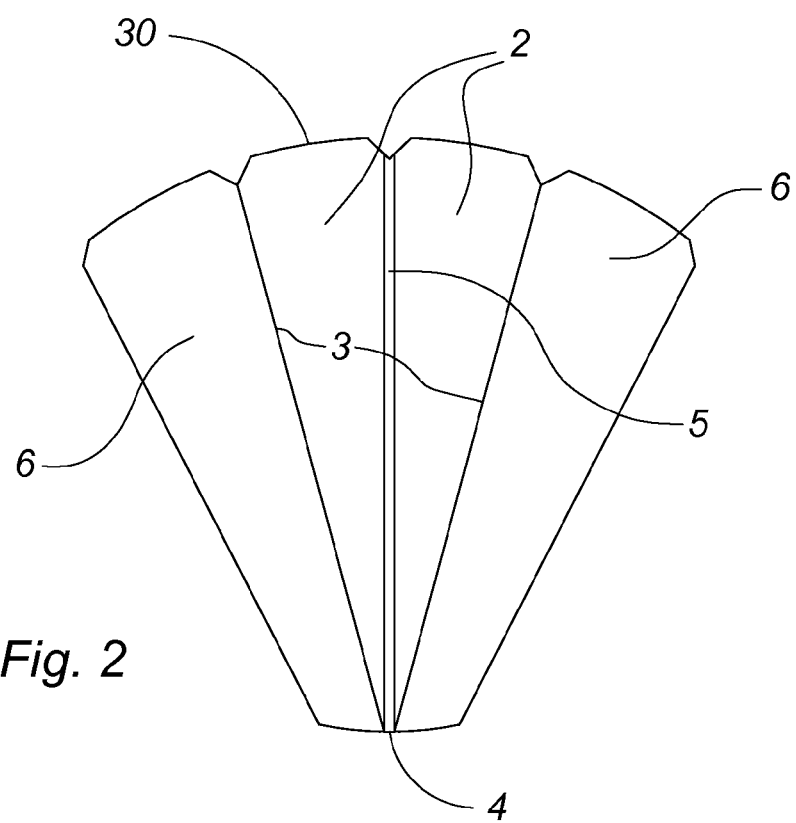
FIG. 2 depicts the stop of FIG. 1 with the protective layers removed.
Figure 3:
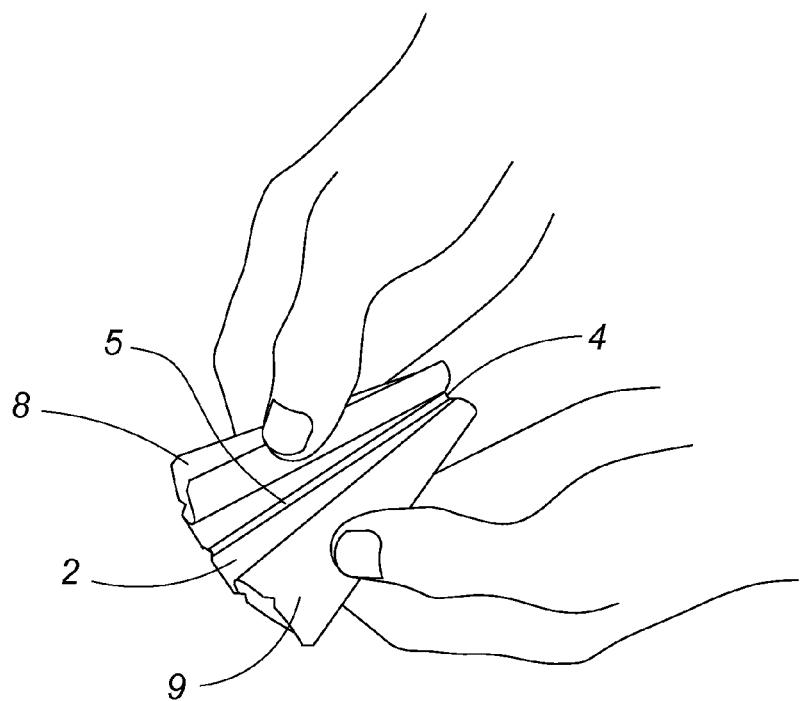
FIG. 3 depicts a user removing the protective layers.
Figure 4:
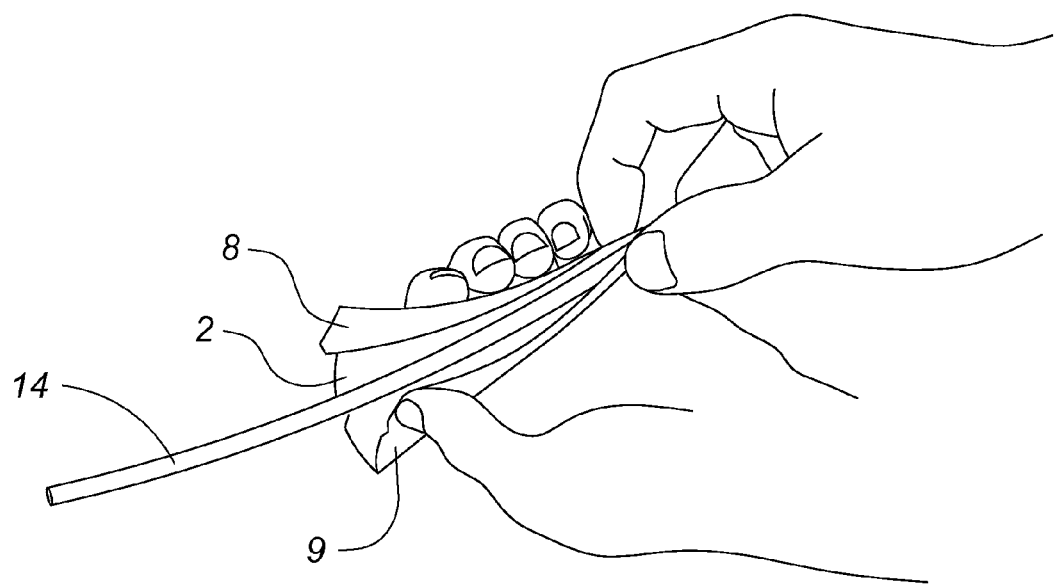
FIG. 4 depicts the stop being applied to a suction catheter.

The present invention relates to a catheter stop that prevents a suction catheter 14 from being overextended into a tracheal tube 40. Referring specifically to FIGS. 1-4, a first embodiment 1 includes a triangular pad 2 having a pair of opposing longitudinal side edges 3 that converge from a base edge 30 toward an apex 4. The pad may have a groove 5 formed on an upper surface for accommodating a catheter when the device is installed as set forth below. Extending from each side edge is an adhesive, triangular wing 6 having a removable protective layer superimposed thereon. Preferably, a first protective layer 8 is likewise triangular and overlays the entire wing and a portion of the pad. Likewise, a second triangular protective layer 9 overlays the entirety of the opposing wing, a portion of the pad and possibly a portion of the first protective layer.

To install the above described embodiment, a user partially separates the two protective layers to fully expose the pad; the pad is positioned on the catheter such that the base edge of the pad is located at the maximum acceptable insertion point of the catheter with the apex pointed upwardly. One of the protective layers is completely removed and the corresponding wing is wrapped about the catheter and adhesively attached thereto. Similarly, the other layer is removed and the opposing wing is wrapped about the catheter and secured.

Now referring to FIGS. 5-8, a second embodiment includes a triangular housing 10 formed of a pair of hinged sections 12 that open and close in a clamshell-type fashion. Each section includes a longitudinal, semi-cylindrical, central bore 13 that cooperates with the bore on the other section to form a tubular passageway when the sections are closed. The passageway is dimensioned to lightly grip a suction catheter 14 having a discrete diameter without compressing or constricting its interior passageway. As such, the grip is further enhanced by a medical adhesive applied to each bore. Reinforcing ribs 15 extend from each bore to opposing edges of the housing section to enhance the structural integrity thereof.

A clamp 16 on an edge of one section detachably engages a latch 17 on the corresponding edge of the other section to secure the housing about a suction catheter. A knurled thumb tab 18 on the front surface of the housing assists a user with repositioning the device.

Accordingly, a caregiver determines the position on the suction catheter that represents the maximum acceptable insertion depth. The housing sections are then fastened about the catheter at the selected position. The housing securely grips the catheter to prevent the catheter from being extended beyond the maximum acceptable insertion depth.

Finally, referring specifically to FIG. 9, the housing 10 may include a trapezoidal lower section 50 with a tapering tubular section 51 depending therefrom; the lower section is substantially planar and has a rectangular cross-section so as not to obstruct airflow through the tracheal tube when resting thereon. The tubular section provides a handle that allows a user to twirl both the housing and catheter during insertion and retraction, which cleanses the inner wall of the tracheal tube to comport with widely-accepted medical procedures.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The invention claimed is:

1. In combination with a tracheal tube configured for insertion into a patient, said tracheal tube having an entrance with a predefined dimension, and a suction catheter inserted into said entrance, a device for limiting a maximum insertion depth of said catheter into said tube comprising:
    an obstruction having a geometric dimension that is greater than said predefined dimension such that said obstruction cannot completely enter said tracheal tube, said obstruction being a triangular pad having a pair of opposing longitudinal side edges that converge from a base edge;
    means for attaching said obstruction to a desired location on said catheter, said means for attaching comprising a first adhesive wing extending from one said side edges and a second adhesive wing extending from another of said side edges.

2. The device according to claim 1 wherein said wing has a removable protective layer superimposed thereon.

3. The device according to claim 1 wherein said first wing has a first protective layer superimposed thereon, said first layer overlaying an entirety of said first wing and a portion of said pad, said second wing having a second protective layer superimposed thereon, said second protective layer overlaying an entirety of said second wing and a portion of said pad.

4. The device according to claim 1 wherein said pad has a groove formed on an upper surface for accommodating said catheter.

5. In combination with a tracheal tube configured for insertion into a patient, said tracheal tube having an entrance with a predefined dimension, and a suction catheter inserted into said entrance, a device for limiting a maximum insertion depth of said catheter into said tube comprising:
    an obstruction having a geometric dimension that is greater than said predefined dimension such that said obstruction cannot completely enter said tracheal tube, said obstruction formed of a triangular housing having a pair of hinged sections that open and close in a clamshell-type fashion;
    means for attaching said obstruction to a desired location on said catheter.

6. The device according to claim 5 wherein said means for attaching said obstruction to a desired location on said catheter comprises a clamp on an edge of one of said sections that releasably engages a latch on an edge of another of said sections to secure the housing about said catheter.

7. The device according to claim 5 wherein each of said sections includes a bore, said bore on one of said sections cooperating with said bore on another of said sections to form a tubular passageway when said sections are closed, said passageway dimensioned to lightly grip said catheter.

8. The device according to claim 7 wherein said bore has an adhesive applied thereto.

9. The device according to claim 7 further comprising reinforcing ribs extending outwardly from said bore to structurally enhance said housing.

10. The device according to claim 5 further comprising a knurled thumb tab on an exterior surface of said housing to assist a user with repositioning said obstruction.

* * * * *